United States Patent
Hamada

(10) Patent No.: US 8,224,138 B2
(45) Date of Patent: Jul. 17, 2012

(54) DENTAL LASER RADIATION CHIP

(75) Inventor: Kazunori Hamada, Kyoto (JP)

(73) Assignee: J. Morita Mfg. Corporation, Kyoto-Shi (JP)

(*) Notice: Subject to any disclaimer, the term of this patent is extended or adjusted under 35 U.S.C. 154(b) by 176 days.

(21) Appl. No.: 12/885,278

(22) Filed: Sep. 17, 2010

(65) Prior Publication Data

US 2011/0229841 A1    Sep. 22, 2011

(30) Foreign Application Priority Data

Sep. 18, 2009   (JP) ................... 2009-217570

(51) Int. Cl.
*G02B 6/26* (2006.01)
*A61N 5/067* (2006.01)

(52) U.S. Cl. .............. 385/38; 385/43; 385/31; 385/123; 433/29

(58) Field of Classification Search ............ 385/12, 385/123, 31, 38, 43, 115, 116, 117; 433/29
See application file for complete search history.

(56) References Cited

U.S. PATENT DOCUMENTS

| | | | | |
|---|---|---|---|---|
| 4,693,552 A | * | 9/1987 | Jeskey | 385/116 |
| 5,030,093 A | * | 7/1991 | Mitnick | 433/164 |
| 5,196,005 A | * | 3/1993 | Doiron et al. | 606/7 |
| 5,976,175 A | * | 11/1999 | Hirano et al. | 607/89 |
| 6,004,315 A | * | 12/1999 | Dumont | 606/15 |
| 2005/0105877 A1 | * | 5/2005 | Nappi et al. | 385/140 |
| 2005/0185260 A1 | * | 8/2005 | Galvanauskas et al. | 359/341.1 |
| 2008/0019657 A1 | * | 1/2008 | Maitland et al. | 385/140 |
| 2011/0212411 A1 | * | 9/2011 | Sinofsky | 433/29 |
| 2011/0229841 A1 | * | 9/2011 | Hamada | 433/29 |

FOREIGN PATENT DOCUMENTS

JP   07-155335 A   6/1995
JP   2000-304948 A   11/2000

OTHER PUBLICATIONS

English abstract of JP2000304948(A) published on Nov. 2, 2000, espacenet database, 1 page.
English abstract of JP7155335(A) published on Jun. 20, 1995, espacenet database, 1 page.

* cited by examiner

*Primary Examiner* — Brian Healy
(74) *Attorney, Agent, or Firm* — Osha Liang LLP

(57) ABSTRACT

A dental laser radiation chip includes an optical fiber including a fiber center section having a core and a clad and also including a jacket for covering the fiber center section. The dental laser radiation chip radiates a laser light having a wavelength of around 3 μm. A tip section of the dental laser radiation chip has a shape of frustum tapering forward in an axial direction. The shape of frustum includes a tip face from which forward laser light is to be radiated forward in the axial direction and an inclining side face from which side laser light is to be radiated in a radial direction with respect to the axial direction. The tip face is mirror-surface-finished to have a surface roughness of 0.008 μm. The inclining side face is rough-surface-finished to have a surface roughness of 0.4 μm.

4 Claims, 12 Drawing Sheets
(1 of 12 Drawing Sheet(s) Filed in Color)

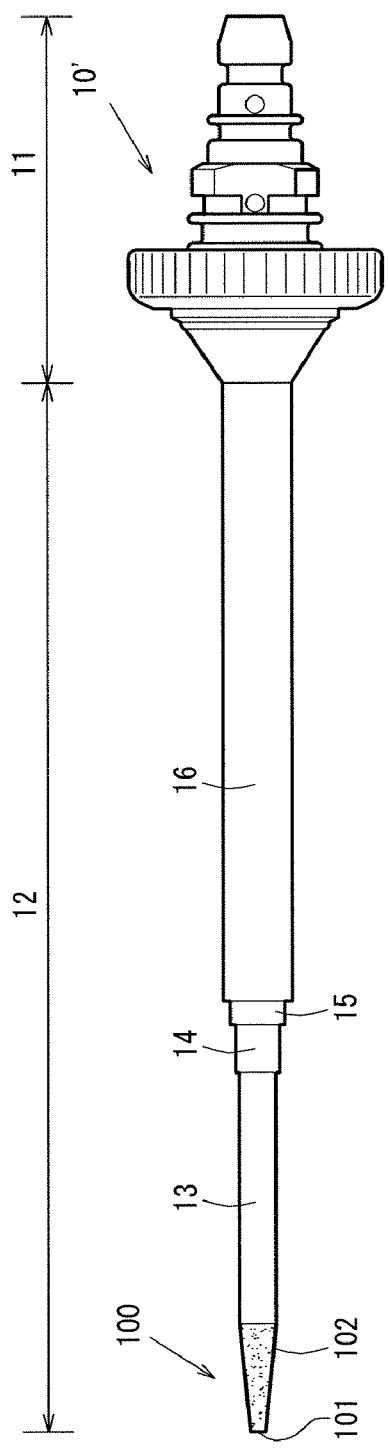
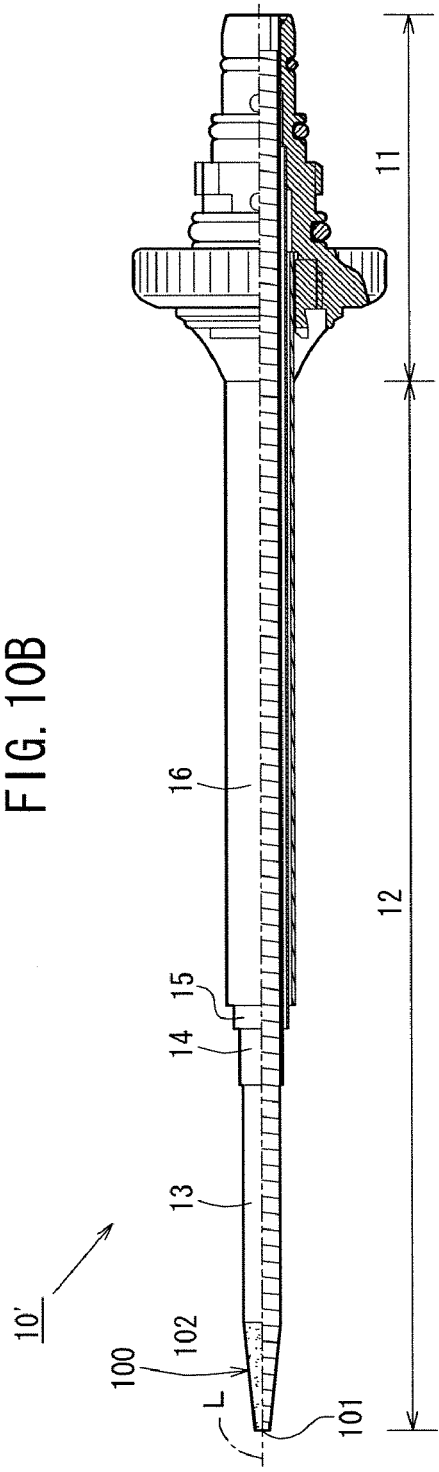
FIG. 10A
FIG. 10B

DENTAL LASER RADIATION CHIP

BACKGROUND OF THE INVENTION

1. Field of the Invention

The present invention relates to a dental laser radiation chip which radiates laser light for dental treatment.

2. Description of the Prior Art

Conventionally, laser light has been used for treatment of wounds such as coagulation, hemostasis, transpiration, ablation, incision or the like. Laser light is also frequently used for dental treatment on small wounds, and a laser radiation chip usable for radiating laser light efficiently in a suitable manner to each of various types of treatment has been proposed (see Patent Document 1).

Patent Document 1 explains that the laser radiation chip described therein has a conical tip and so laser light can be radiated to a wound positioned forward with respect to the chip efficiently, namely, at a high energy density.

Meanwhile, according to a conventional method for treating, for example, periodontal diseases which constitute one of the biggest causes by which the Japanese people lose their teeth, it is necessary to remove unhealthy granulation from a narrow and deep periodontal pocket and tartar from a wide area and also to perform disinfection over a wide area. This is technically difficult and imposes a heavy load on the operator and the patient.

Even if, for example, the laser radiation chip described in Patent Document 1 is used for periodontal diseases which require a high level of technique for treatment, it is difficult to efficiently perform removal of unhealthy granulation from a narrow and deep periodontal pocket and removal of tartar from a wide area and to perform disinfection over a wide area at the same time. No satisfactory result has been provided for the operator or the patient.

Patent Document 1: Japanese Laid-Open Patent Publication No. 2000-304948

SUMMARY OF THE INVENTION

One or more embodiments of the present invention provide a dental laser radiation chip which is capable of efficiently providing, at the same time, an effect of removing tartar and unhealthy granulation, an effect of disinfection and an effect of planing even when the site for operation is narrow.

One or more embodiments of the present invention are directed to a dental laser radiation chip, comprising an optical fiber including a fiber center section having a core and a clad and also including a jacket for covering the fiber center section, the dental laser radiation chip being for radiating laser light having a wavelength of around 3 μm. A tip section of the dental laser radiation chip has a shape of frustum tapering forward in an axial direction, the shape of frustum including a tip face from which the laser light is to be radiated forward in the axial direction and an inclining side face from which the laser light is to be radiated in a radial direction with respect to the axial direction. The tip face is mirror-surface-finished, and the inclining side face is rough-surface-finished.

The laser light having a wavelength of around 3 μm as described above may be Er:YAG laser light (erbium YAG laser; wavelength: about 2.94 μm) or Er.Cr;YSGG laser (wavelength: about 2.78 μm) both having a high absorbability to water and a relatively high degree of safety.

The shape of frustum may be a shape of frustum of cone, a shape of frustum of triangular pyramid, a shape of frustum of quadrangular pyramid or a shape of frustum of polygonal pyramid.

The tip face may be perpendicular to the axial direction or slightly inclined from the perpendicular direction with respect to the axial direction. The tip face may be flat or curved, i.e., convexed or concaved with respect to the axial direction.

The inclining side face may be a flat face as seen from the side, a face curved to be projected outward in a radial direction with respect to the axial direction as seen from the side, or a face curved to be concaved inward in the radial direction with respect to the axial direction as seen from the side.

According to the structure of one or more embodiments of the present invention, laser light having a high energy density is radiated forward in the axial direction from the tip face, while laser light having a low energy density is radiated from the inclining side face over a wide area in a radial direction with respect to the axial direction. Due to this, an effect of removing tartar and unhealthy granulation, an effect of disinfection and an effect of planing (an effect provided by smoothing the surface of the tooth; specifically including an effect provided by root planing of smoothing the convexed and concaved portions formed on the surface of the root of the tooth after the tartar is removed) are efficiently provided at the same time.

More specifically, the tip section of the dental laser radiation chip is formed to have a shape of frustum tapering forward in the axial direction, and the tip face from which the laser light is to be radiated forward in the axial direction is mirror-surface-finished. Due to this, the laser light of a wavelength of around 3 μm which has a high absorbability to water and a relatively high degree of safety can be radiated forward in the axial direction in a state of a high energy density. This provides a superb effect of removing tartar and unhealthy granulation.

The term "axial direction" is the height direction of the shape of frustum, and the term "forward in the axial direction" means outward to the shape of tapering frustum along the height direction.

The inclining side face which is a part of the shape of tapering frustum is rough-surface-finished. Due to this, the laser light is scattered by the convexed and concaved portions on the inclining side face formed by roughening. Therefore, the laser light having a low energy density can be radiated over a wide area in a radial direction with respect to the axial direction. Due to this, an effect of disinfection over a wide area and an effect of efficient planing can be provided. Especially the effect of disinfection is superb so that bacteria concealed in a huge number of craters on the surface of the tooth can be killed.

Thus, the dental laser radiation chip of the present invention efficiently provides an effect of removing tartar and unhealthy granulation, an effect of disinfection and an effect of planing at the same time.

In an embodiment of the present invention, the shape of frustum may be a shape of frustum of cone, the mirror-surface-finished face may have a surface roughness of 0.1 μm or less, and the rough-surface-finished face may have a surface roughness of 0.2 μm or greater and 20 μm or less.

Due to the structure of the present invention, the operability can be improved, and also an effect of removing tartar and unhealthy granulation, an effect of disinfection and an effect of planing can be provided more efficiently and certainly.

More specifically, the tip section of the dental laser radiation chip has a shape of frustum of cone. Due to this, there is no directivity with respect to the axial direction which might otherwise be caused due to the shape of the tip section, and the tip section is easily shaped along the surface of the tooth, especially the surface of the root of the tooth. Thus, the operability especially in a narrow site for operation can be improved.

The mirror-surface-finished face has a surface roughness of 0.1 µm or less. Due to this, the laser light having a higher energy density can be radiated forward in the axial direction. More specifically, in the case where the tip face is mirror-surface-finished to have a surface roughness of greater than 0.1 µm, the laser light is scattered by the microscopic convexed and concaved portions having a surface roughness of greater than 0.1 µm which are formed on the surface of the tip face, and so the laser light having a desired energy density cannot be radiated. By mirror-surface-finishing the tip face to have a surface roughness of 0.1 µm or less, the scattering of the laser light on the surface of the tip face is suppressed, and the laser light having a high energy density and so having a superb performance of removing tartar and unhealthy granulation can be radiated more certainly.

The rough-surface-finished face has a surface roughness of 0.2 µm or greater and 20 µm or less. Due to this, the laser light having an energy density suitable to perform disinfection and planing without unnecessarily damaging a soft tissue can be radiated over a sufficiently wide area because of the convexed and concaved portions of the size range mentioned above which are formed on the rough-surface-finished face.

More specifically, in the case where the inclining side face is rough-surface-finished to have a surface roughness of less than 0.2 µm, the laser light is not sufficiently scattered due to the convexed and concaved portions having a surface roughness of less than 0.2 µm on the surface of the inclining side face. Therefore, the laser light having an energy density of a level at which a soft tissue is not unnecessarily damaged cannot be radiated over a wide area.

By contrast, in the case where the inclining side face is rough-surface-finished to have a surface roughness of greater than 20 µm, the laser light is excessively scattered due to the convexed and concaved portions on the inclining side face. As a result, the energy density is reduced, and so the laser light having desired effects of disinfection and planing cannot be radiated.

As understood from the above, by rough-surface-finishing the inclining side face to have a surface roughness of 0.2 µm or greater and 20 µm or less, the laser light having an energy density suitable to perform disinfection and planing without unnecessarily damaging a soft tissue can be radiated over a sufficiently wide area.

In an embodiment of the present invention, the tip section of the dental laser radiation chip may have a shape of frustum having a height in the axial direction of 2 mm or greater and 5 mm or less and a cone angle of 5 degrees of greater and 20 degrees or less.

Due to the structure of the present invention, even when the site for operation is narrow and deep like, for example, a periodontal pocket, the tip section of the dental laser radiation chip can be inserted into the site for operation to radiate laser light having sufficient effects of removing tartar and unhealthy granulation, of disinfection and of planing.

More specifically, the height in the axial direction of the tip section having a shape of frustum is set to 2 mm or greater and 5 mm or less. Due to this, the tip section can be inserted into a narrow and deep site for operation having a depth of about 2 to 5 mm, for example, a periodontal pocket, and so the laser light having sufficient effects of removing tartar and unhealthy granulation, of disinfection and of planing can be radiated to realize efficient treatment.

Furthermore, in the case where the height in the axial direction of the tip section having a shape of frustum is set to less than 2 mm, the tip section cannot be inserted deeply into a narrow and deep site for operation, for example, a periodontal pocket. Therefore, the radiated laser light cannot reach the vicinity of the bottom thereof, and so the treatment cannot be performed sufficiently. In addition, since the area size of the inclining side face is decreased, the amount of radiation of the laser light having an energy density suitable to perform disinfection and planing is decreased and so neither the effect of disinfection nor the effect of planing can be provided sufficiently.

By contrast, in the case where the height in the axial direction of the tip section having a shape of frustum is greater than 5 mm, the area size of the inclining side face is increased. Therefore, the amount of the laser light radiated from the inclining side face is increased, and so the amount of radiation of the laser light radiated from the tip section which has a high energy density and so has a superb performance of removing tartar and unhealthy granulation is decreased.

As will be understood from the above, by setting the height in the axial direction of the shape of frustum to 2 mm or greater and 5 mm or less, the tip section can be inserted into a narrow an deep site for operation having a depth of about 2 to 5 mm, for example, a periodontal pocket, and so the laser light providing sufficient effects of removing tartar and unhealthy granulation, of disinfection and of planing at the same time can be radiated to realize efficient treatment.

In addition to setting the height in the axial direction of the tip section having a shape of frustum to 2 mm or greater and 5 mm or less, the cone angle of the shape of frustum is set to 5 degrees or greater and 20 degrees or less. Due to this, the tip section can be inserted into a narrow and deep site for operation, for example, a periodontal pocket to perform an operation certainly and improve the durability.

More specifically, in the case where the height in the axial direction of the shape of frustum is set to the range described above and the cone angle of the shape of frustum is set to less than 5 degrees, a required area size of radiation from the tip face cannot be obtained, and so the amount of radiation of the laser light having a high energy density and so having a superb performance of removing tartar and unhealthy granulation is decreased. In the case where the cone angle of the tip section having a shape of frustum is less than 5 degrees, the tip section of the dental laser radiation chip is excessively thin and a sufficient durability against repeated operations cannot be provided.

By contrast, in the case where the height in the axial direction of the tip section having a shape of frustum is set to the range described above and the cone angle thereof is set to greater than 20 degrees, the tip section of the dental laser radiation chip is excessively thick and cannot be inserted up to the vicinity of the bottom of a narrow and deep site for operation. Therefore, the laser light having a high energy density does not reach the vicinity of the bottom of the site for operation, for example, a periodontal pocket, and so the performance of removing tartar and unhealthy granulation is deteriorated.

As will be understood from the above, by setting each of the height and the cone angle of the tip section having a shape of frustum to the above-described range, the durable tip section of the dental laser radiation chip can be inserted up to the vicinity of the bottom of a narrow and deep site for operation, for example, a periodontal pocket. Therefore, the laser light having a high energy density and so having a superb performance of removing tartar and unhealthy granulation can be radiated from the tip face, and the laser light having sufficient effects of disinfection and planing can be radiated from the inclining side face. Thus, efficient treatment which provides an effect of removing tartar and unhealthy granulation, an effect of disinfection and an effect of planing at the same time can be performed.

Thus, one or more embodiments of the present invention provide a dental laser radiation chip which is capable of efficiently providing an effect of removing tartar and unhealthy granulation, an effect of disinfection and an effect planing at the same time even when the site for operation is narrow.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 10A is a side view of a dental laser radiation chip in another embodiment.

FIG. 10B is a partially cut cross-sectional view of the dental laser radiation chip in another embodiment.

DESCRIPTION OF THE PREFERRED EMBODIMENTS

Hereinafter, an embodiment of the present invention will be described with reference to the drawings.

Figure 1:
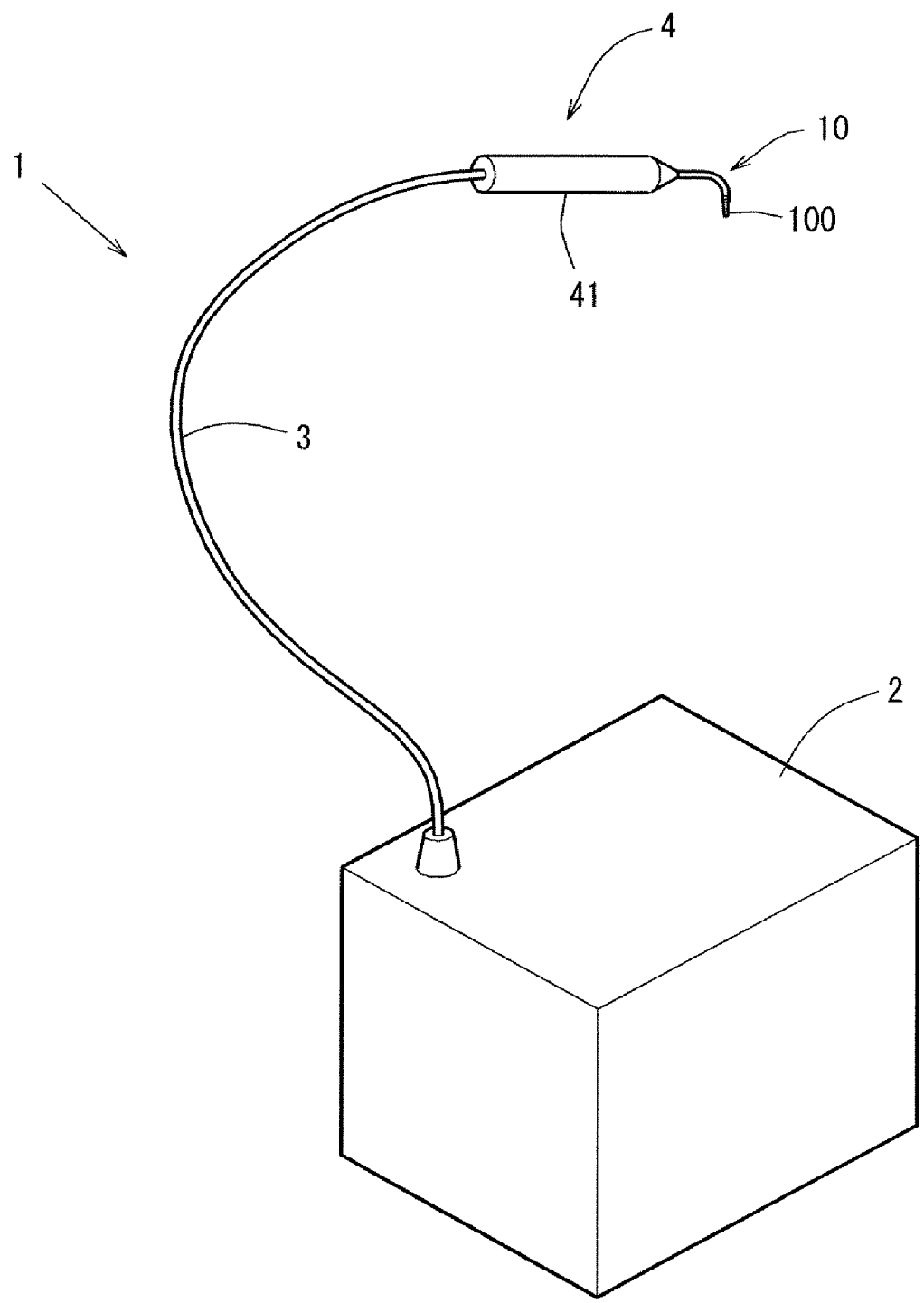
FIG. 1 is an isometric view of a laser treatment apparatus.
Figure 2:
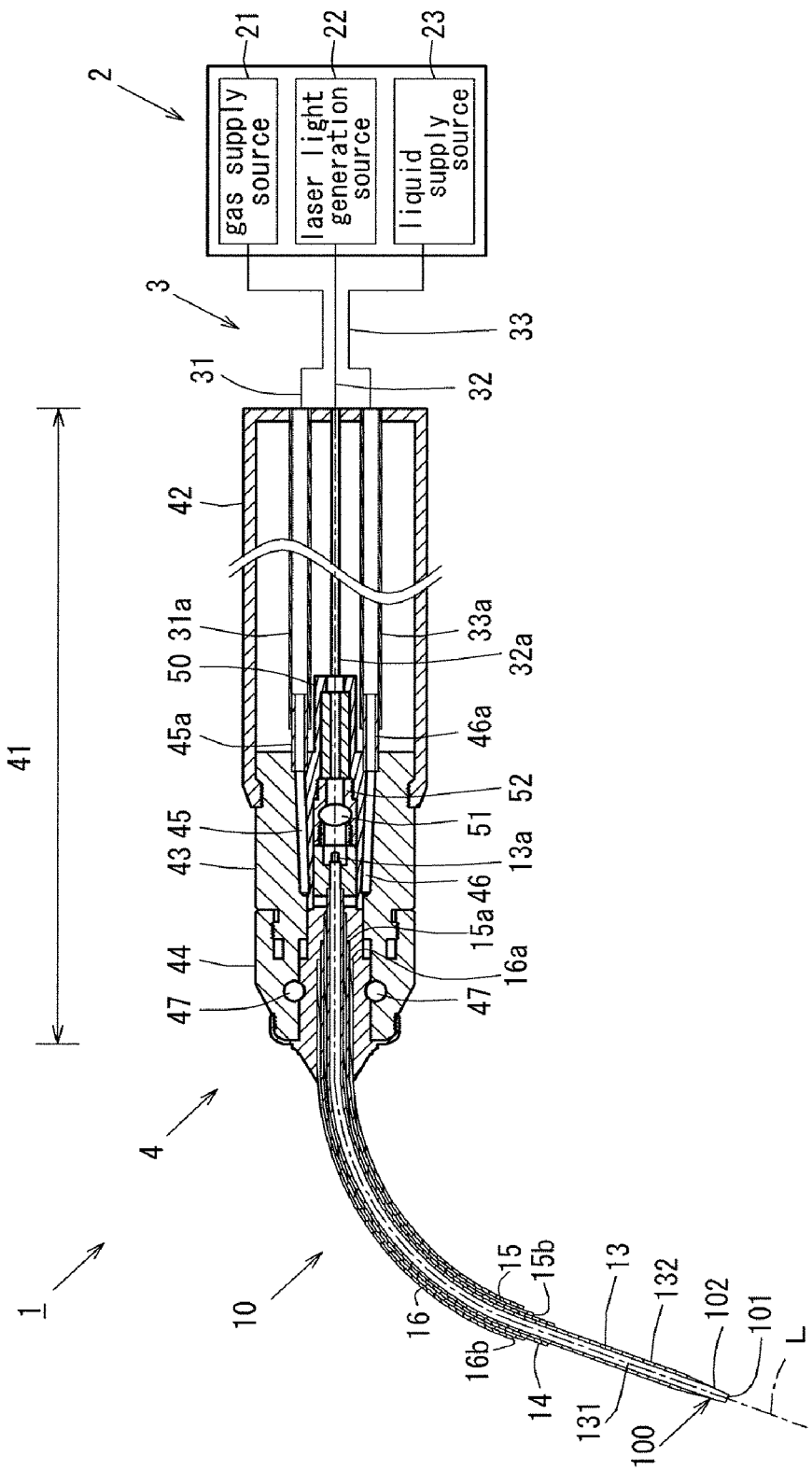
FIG. 2 is a schematic view illustrating the laser treatment apparatus and a hand piece.
Figure 3:
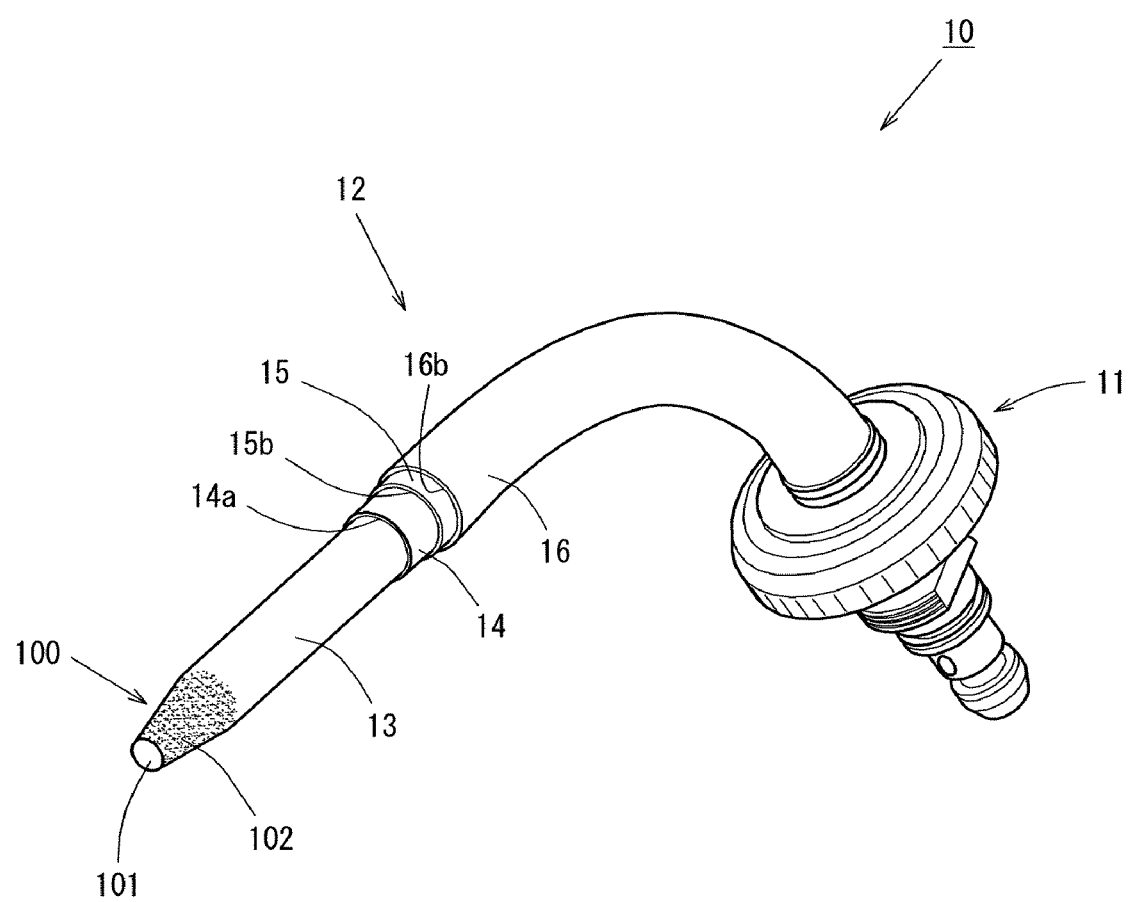
FIG. 3 is an isometric view of a dental laser radiation chip.
Figure 4:
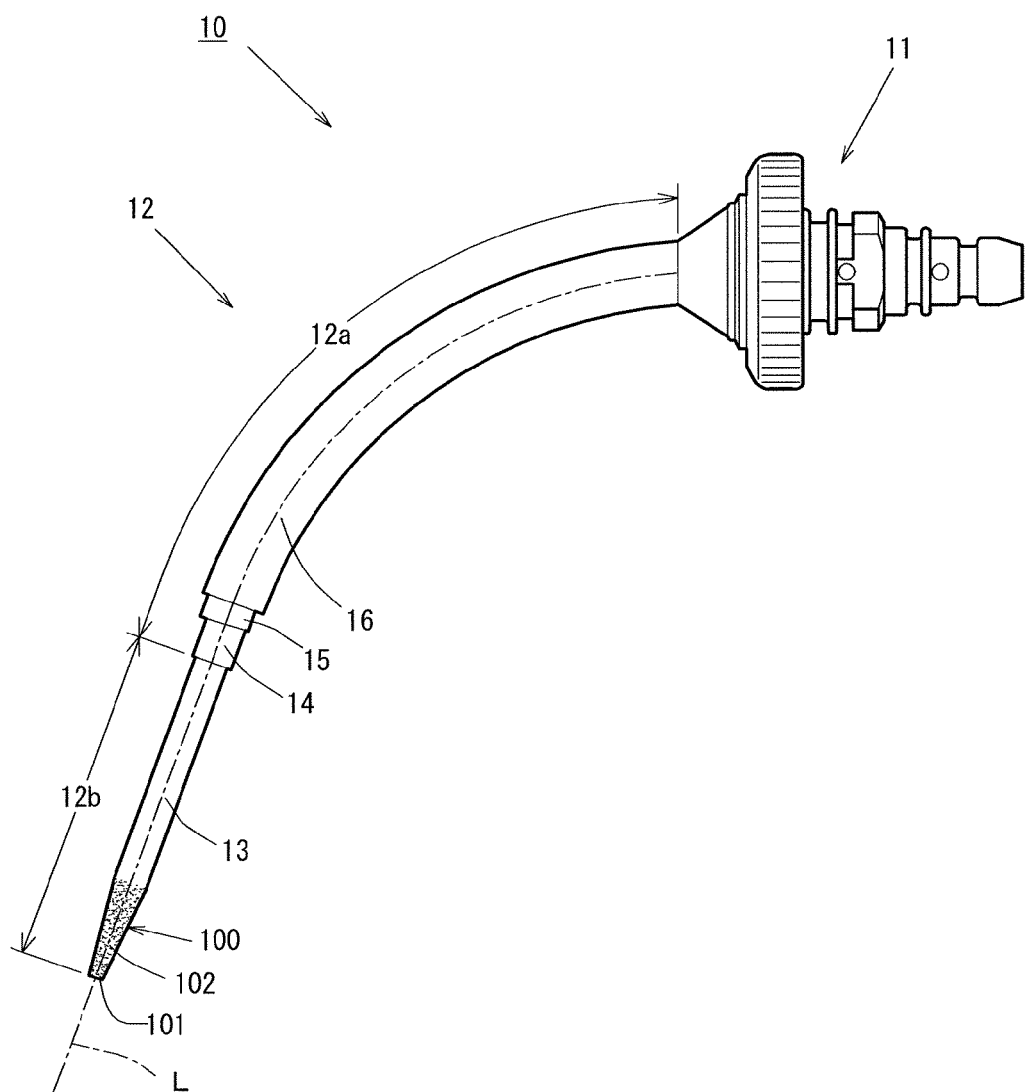
FIG. 4 is a side view of the dental laser radiation chip.
Figure 5A:
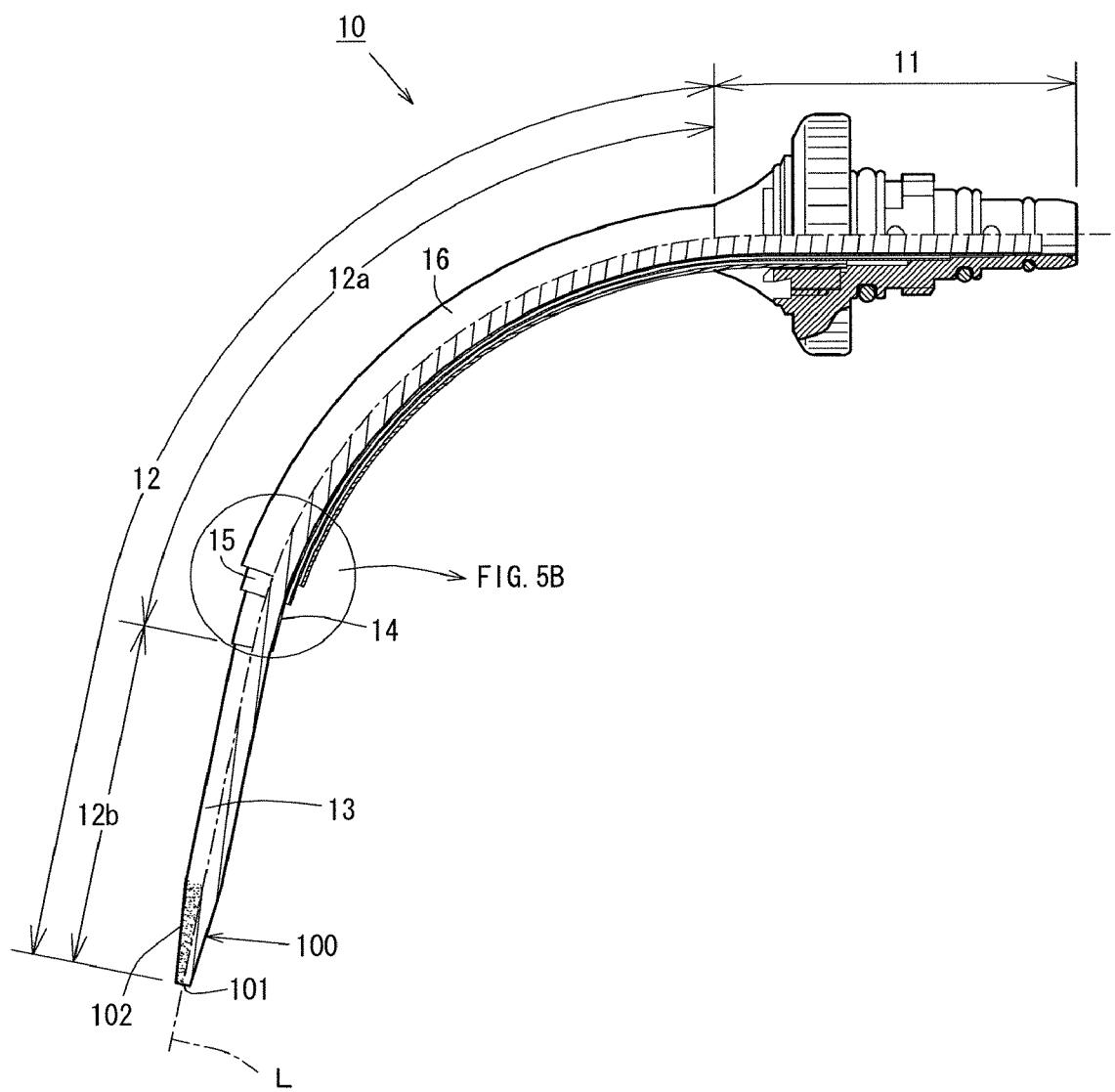
FIG. 5A is a partially cut cross-sectional view of the dental laser radiation chip.
Figure 5B:
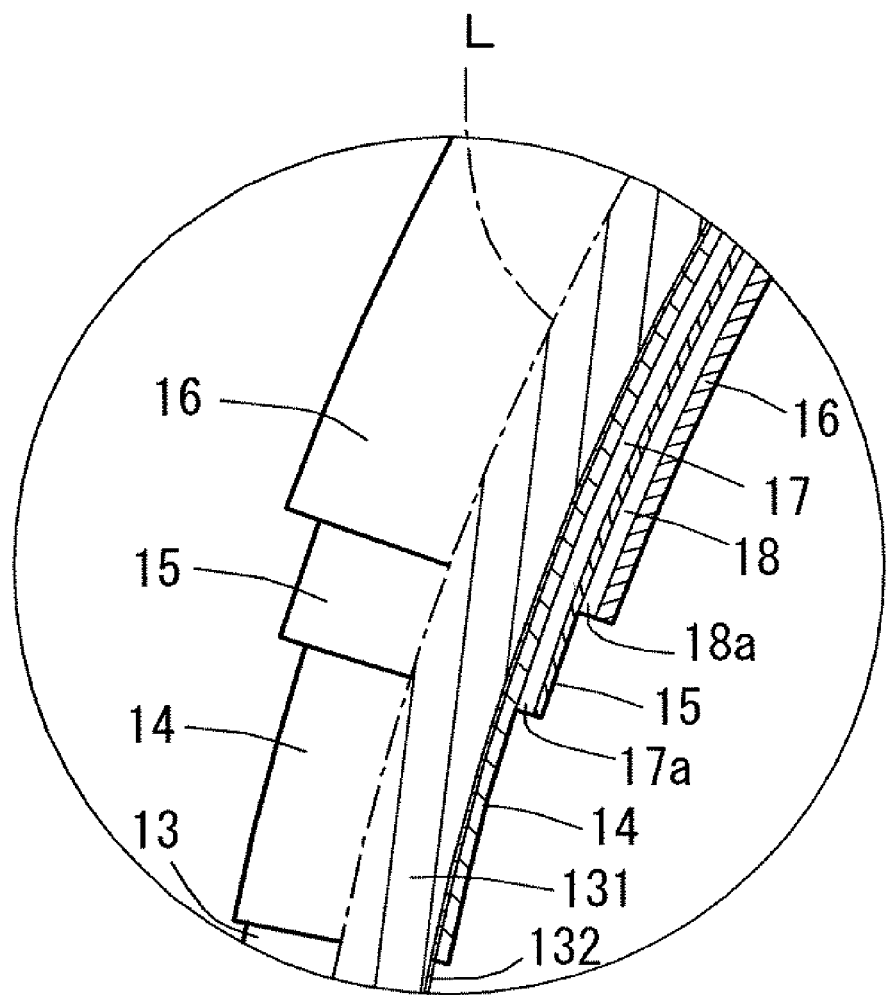
FIG. 5B is a view of an enlarged portion of FIG. 5A.
Figure 6A:
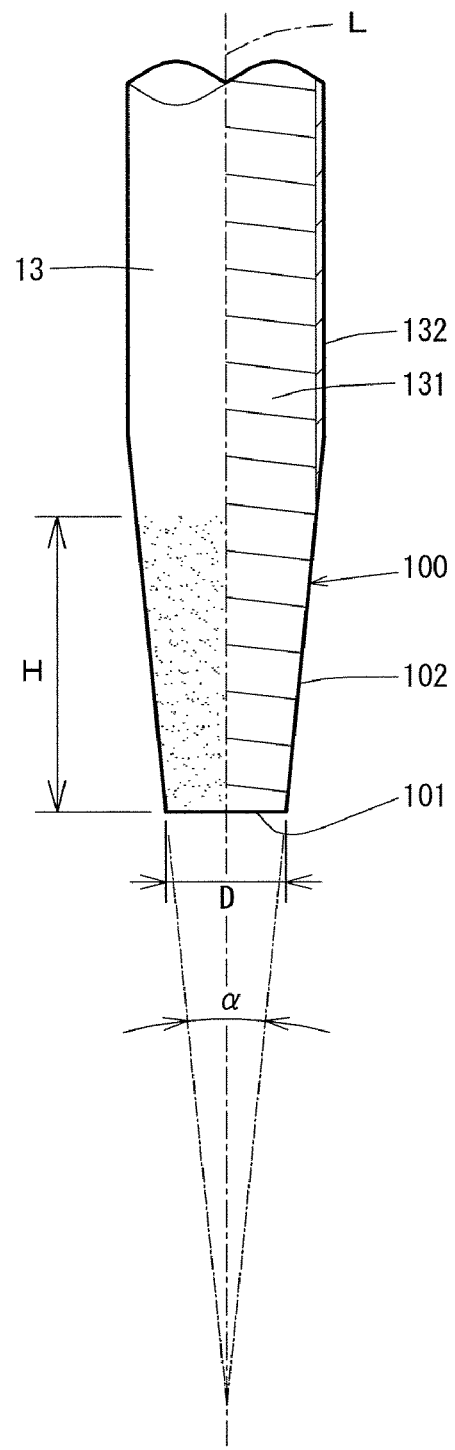
FIG. 6A provides a view illustrating a shape of a tip of an exit tip.
Figure 6B:
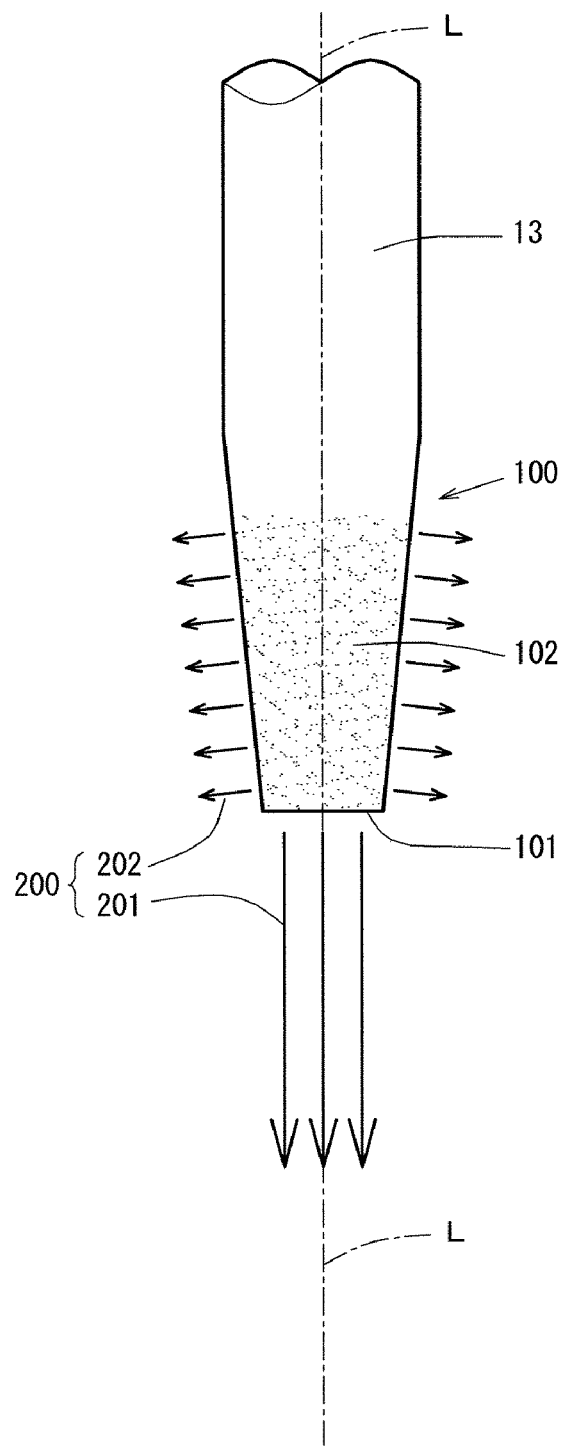
FIG. 6B provides a view illustrating a radiation direction of Er:YAG laser light from the exit tip.
Figure 7:
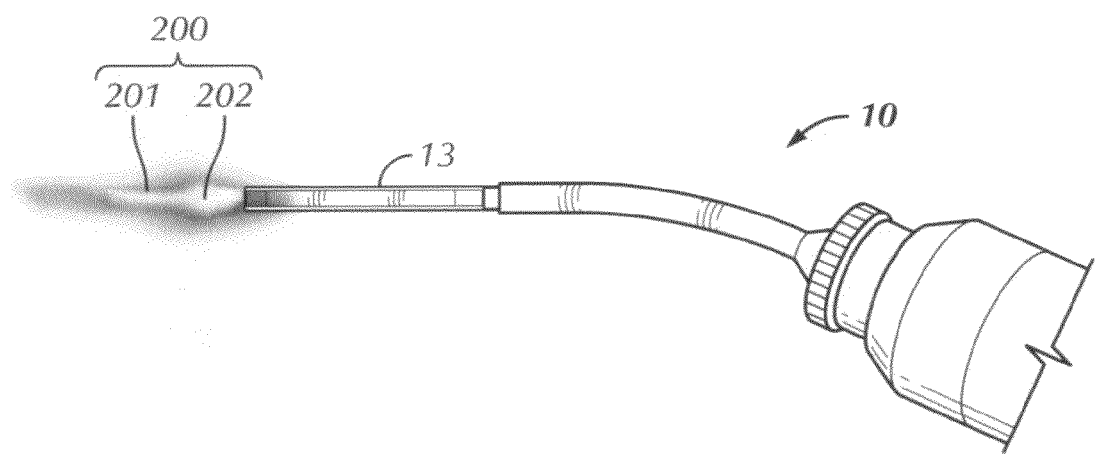
FIG. 7 is a photo illustrating a radiation state of the Er:YAG laser light from the dental laser radiation chip.

FIG. 1 is an isometric view of a laser treatment apparatus 1, and FIG. 2 is a schematic view illustrating the laser treatment apparatus 1 and a hand piece 4. FIG. 3 is an isometric view of a dental laser radiation chip 10, and FIG. 4 is a side view thereof. FIG. 5A is a partially cut cross-sectional view of the dental laser radiation chip 10, and FIG. 5B is a view of an enlarged portion of FIG. 5A. FIG. 7 is a photo illustrating a radiation state of Er:YAG laser light 200 from the dental laser radiation chip 10. FIG. 6A illustrates the shape of a tip of the exit tip 100, and FIG. 6B illustrates the radiation direction of the Er:YAG laser light 200 from the exit tip 100.

The laser treatment apparatus 1 includes a treatment apparatus main body 2, the laser hand piece 4, and a medium supply cable 3 for connecting the treatment apparatus main body 2 and the laser hand piece 4.

As shown in FIG. 2, the treatment apparatus main body 2 has built therein a gas supply source 21 for supplying a gas such as air, inert gas or the like, a laser light generation source 22 for generating Er:YAG laser light, and a liquid supply source 23 for supplying a liquid such as water, physiological saline solution or the like.

The gas supplied from the gas supply source 21, the Er:YAG laser light emitted by the laser light generation source 22, and the liquid supplied from the liquid supply source 23 are supplied to the hand piece 4 via the medium supply cable 3.

The medium supply cable 3 includes a gas supply pipe 31 acting as a flow path for supplying a gas, an optical transmitter 32 formed of an optical fiber, and a liquid supply pipe 33 acting as a flow path for supplying a liquid. The optical transmitter 32 may be solid or hollow as long as having a transmission efficiency suitable for the type of laser light to be transmitted.

An end of the gas supply pipe 31 on the side of the treatment apparatus main body 2 is connected to the gas supply source 21, and an opposite end 31a of the gas supply pipe 31 is inserted into, and connected to, the hand piece 4. Similarly, an end of the optical transmitter 32 on the side of the treatment apparatus main body 2 is connected to the laser light generation source 22, and an opposite end 32a of the optical transmitter 32 is inserted into, and connected to, the hand piece 4. An end of the liquid supply pipe 33 on the side of the treatment apparatus main body 2 is connected to the liquid supply source 23, and an opposite end 33a of the liquid supply pipe 33 is inserted into, and connected to, the hand piece 4.

The laser hand piece 4 includes a hand piece main body 41 to be held by the operator and a dental laser radiation chip 10 which is detachably attachable to a tip of the hand piece main body 41.

The hand piece main body 41 includes a hollow cylindrical hand piece housing 42, a cylindrical intermediate member 43 attached forward (leftward in FIG. 2) to the hand piece housing 42, and an attaching mechanism 44 attached forward to the intermediate member 43. The attaching mechanism 44 allows the dental laser radiation chip 10 to be freely attached to, or detached from, the hand piece main body 41. The hand piece housing 42, the intermediate member 43 and the attaching mechanism 44 are located in this order from a rearward position (rightward position in FIG. 2) toward a forward position (leftward position in FIG. 2) in the hand piece.

The hand piece housing 42 has a hollow cylindrical shape and positioned as lying down such that a rear end thereof is closed by a bottom plate. A front end thereof can be screwed with the intermediate member 43. The opposite end 31a of the gas supply pipe 31 is connected to a gas flow path 45 formed in the intermediate member 43 by a connection pipe 45a inside the hand piece housing 42. Similarly, the opposite end 33a of the liquid supply pipe 33 is connected to a liquid flow path 46 formed in the intermediate member 43 by a connection pipe 46a inside the hand piece housing 42. The opposite end 32a of the optical transmitter 32 is connected to a ferrule 50 formed in the intermediate member 43 inside the hand piece housing 42.

The intermediate member 43 has built therein the ferrule 50 located along an axis thereof and the gas flow path 45 and the liquid flow path 46 which are located outer to the ferrule 50.

The ferrule 50 is connected at a rear end thereof to the opposite end 32a of the optical transmitter and has a lens holder 52 attached therein. The lens holder 52 has a lens 51 provided therein.

The lens 51 is located to face the opposite end 32a of the optical transmitter 32 and to collect and guide the laser light from the optical transmitter 32 to the dental laser radiation chip 10.

The gas flow path 45 connected to the opposite end 31a of the gas supply pipe 31 and the liquid flow path 46 connected to the opposite end 33a of the liquid supply pipe 33 extend to a forward position in the intermediate member 43 and are connected to the dental laser radiation chip 10. Due to this structure, the gas supplied from the gas supply source 21 passes the gas supply pipe 31 and the gas flow path 45 and is supplied to the dental laser radiation chip 10. The liquid supplied from the liquid supply source 23 passes the liquid supply pipe 33 and the liquid flow path 46 and is supplied to the dental laser radiation chip 10.

The attaching mechanism 44 screwed and thus attached to a front end of the intermediate member 43 allows the dental laser radiation chip 10 to be freely attachable to or detachable from the intermediate member 43 due to a plurality of stopper spheres 47.

Now, the dental laser radiation chip 10 will be described.

The dental laser radiation chip 10 includes an attachment section 11 to be attached to the intermediate member 43 via the attaching mechanism 44 and a chip main body 12 (see FIG. 5A).

The chip main body 12 includes a fiber 13 located along an axis L thereof, a protective pipe 14 for covering the fiber 13, a hollow first pipe 15 located outer to the protective pipe 14, and a hollow second pipe 16 located outer to the first pipe 15.

The chip main body 12 includes a curved part 12a in which the fiber 13 is covered with the protective pipe 14 and a straight part 12b in which the fiber 13 is exposed from the protective pipe 14.

The fiber 13 is formed of one quartz optical fiber continuous from a rear end of the attachment section 11 (right end in FIG. 5A) to a tip of the chip main body 12. An incidence-side end of the fiber 13 exposed from the attachment section 11 toward the hand piece housing 42 acts as an incidence end 13a (see FIG. 2). A tip-side end of the fiber 13, which is opposite to the hand piece housing 42, acts as an exit tip 100. The material of the optical fiber is not limited to quartz and may be sapphire or the like.

The fiber 13 is a single-core optical fiber and includes a fiber center section 131 existing at the center thereof and formed of a core and a clad, and a jacket 132 for covering the fiber center section 131.

In the straight part 12b, the fiber 13 is not covered with the protective pipe 14 and is exposed.

The incidence end 13a faces the lens 51 inside the intermediate member 43. Therefore, the Er:YAG laser light emitted by the laser light generation source 22 can be incident from the incidence end 13a via the optical transmitter 32, the ferrule 50 and the lens 51, pass the fiber 13 and be radiated from the exit tip 100.

The first pipe 15, from a rear end 15a located inside the attachment section 11 to a front end 15b at which a front end 14a of the protective pipe 14 is partially exposed, is provided so as to enclose the fiber 13 covered with the protective pipe 14.

The second pipe 16, from a rear end 16a located inside the attachment section 11 to a front end 16b at which the front end 15b of the first pipe 15 is partially exposed, is provided so as to enclose the first pipe 15. The protective pipe 14, the first pipe 15 and the second pipe 16 are formed of stainless steel.

The fiber 13, the protective pipe 14 for covering the fiber 13, the first pipe 15 for enclosing the protective pipe 14, and the second pipe 16 for enclosing the first pipe 15 are concentrically located around the axis L as the center.

A clearance between the protective pipe 14 and the first pipe 15 acts as a first flow path space 17, and a clearance between the first pipe 15 and the second pipe 16 acts as a second flow path space 18 (see the enlarged portion FIG. 5B).

The first flow path space 17 is opened at an opening 17a corresponding to the front end 15b of the first pipe 15, and is communicated to the liquid flow path 46 inside the intermediate member 43. Therefore, the liquid supplied from the liquid supply source 23 passes the liquid supply pipe 33, the liquid flow path 46 and the first flow path space 17 and is jetted from the opening 17a.

Similarly, the second flow path space 18 is opened at an opening 18a corresponding to the front end 16b of the second pipe 16, and is communicated to the gas flow path 45 inside the intermediate member 43. Therefore, the gas supplied from the gas supply source 21 passes the gas supply pipe 31, the gas flow path 45 and the second flow path space 18 and is jetted from the opening 18a.

Due to such a structure of the dental laser radiation chip 10, it can be chosen whether to supply liquid via the first flow path space 17 or to supply gas via the second flow path space 18 in accordance with the type of treatment to be performed using the laser treatment apparatus 1. Only the gas, only the liquid or a gas-liquid mixture jettable in a mist-like state may be supplied toward a radiation area of the Er:YAG laser light 200 described later.

Next, the exit tip 100, which is a tip of the fiber 13 in the dental laser radiation chip 10 having the above-described structure will be described in detail.

The exit tip 100, which is a bottom end of the fiber 13 exposed from the protective pipe 14 has a shape of frustum of cone tapering downward, i.e., forward in the direction of the axis L.

More specifically, the exit tip 100 has a shape of frustum of cone including a circular tip face 101 from which laser light 201 for removing tartar and unhealthy granulation is to be radiated downward, i.e., forward in the direction of the axis L (hereinafter, such laser light will be referred to as "forward laser light 201") and an inclining side face 102 from which laser light 202 for disinfection and planing is to be radiated in a radial direction with respect to the axis L (hereinafter, such laser light will be referred to as "side laser light 202").

The exit tip 100 has a shape of frustum of cone having a height H of 2 mm or greater and 5 mm or less, for example, 3 mm, and a cone angle α of 5 degrees or greater and 20 degrees or less, for example, 11 degrees. Due to this, the circular tip face 101 of the fiber 13 having a diameter of 600 μm has a diameter D of 400 μm.

The circular tip face 101 is mirror-surface-finished to have a surface roughness of 0.1 μm or less, for example, 0.008 μm, and the inclining side face 102 is rough-surface-finished to have a surface roughness of 0.2 μm or greater and 20 μm or less, for example, 0.4 μm.

Due to such a structure of the exit tip 100, as shown in FIGS. 6B and 7, the Er:YAG laser light 200 emitted by the laser light generation source 22 and incident from the incidence end 13a via the optical transmitter 32, the ferrule 50 and the lens 51 can be radiated as the forward laser light 201 from the circular tip face 101 downward, i.e., forward in the direction of the axis L, and also radiated as the side laser light 202 from the inclining side face 102 radially with respect to the axis L, i.e., outer in diametrical directions of the exit tip 100.

FIG. 7 is a color drawing showing a state in which visible light used instead of the Er:YAG laser, which has a wavelength in an infrared range and so is invisible, is radiated. This color drawing illustrates how the Er:YAG laser 200 is radiated by the dental laser radiation chip 10.

Figure 8:
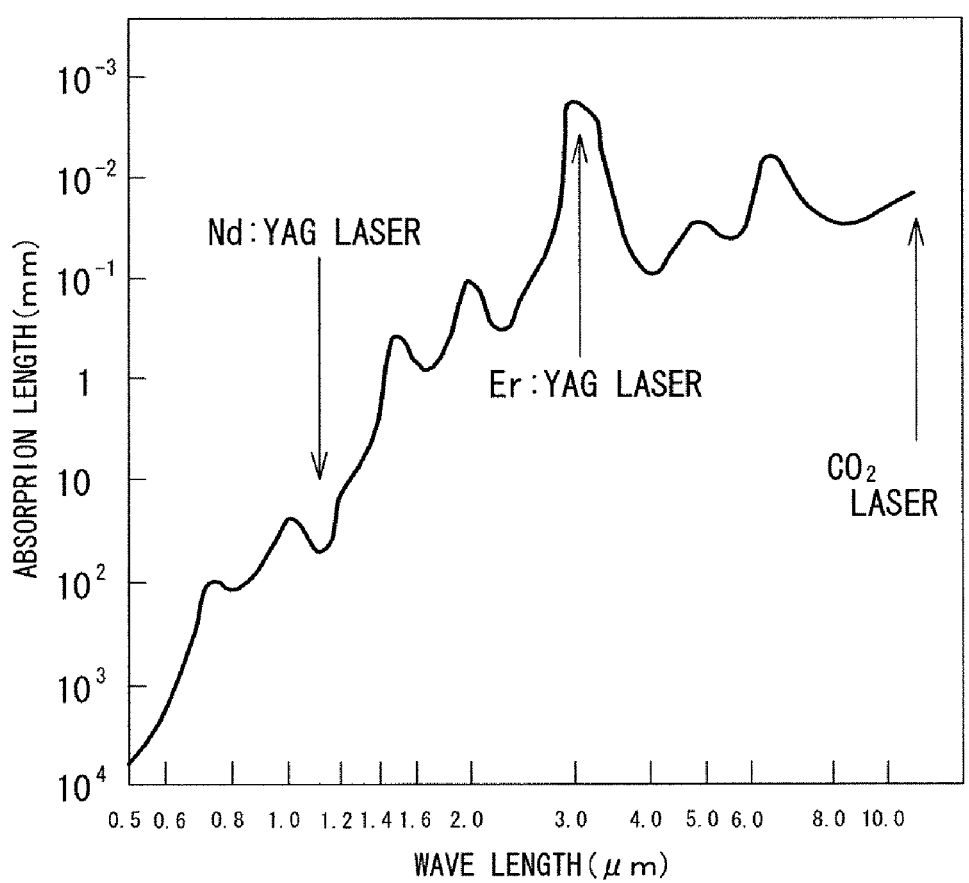
FIG. 8 is an absorption spectral graph of the wavelength of the laser light for water.

Now, the Er:YAG laser 200 emitted by the laser light generation source 22 in this example will be described with reference to FIG. 8. FIG. 8 is an absorption spectral graph of the wavelength of the laser light for water.

Laser light reacts with different substances in accordance with the wavelength thereof. The laser treatment apparatus 1, mainly for treating periodontal diseases, uses the Er:YAG laser light emitted by the laser light generation source 22.

The Er:YAG laser light 200 has a wavelength of about 2.94 μm in the infrared range, and as shown in FIG. 8, has a high absorbability to water.

Such Er:YAG laser light can provide an effect of removing tartar and unhealthy granulation, an effect of disinfection and an effect of planing with an energy generated when the laser light reacts with water molecules and transpires (microexplosion). The Er:YAG laser light transpires only in a surface layer and has a low radiation energy density in an area peripheral to the radiation field, and so has little influence on the peripheral tissues and is highly safe.

Instead of the Er:YAG laser light, Er-based laser light having a wavelength of around 3 μm, for example, Er.Cr;YSGG laser light having a wavelength of about 2.78 μm may be used.

Figure 9A:
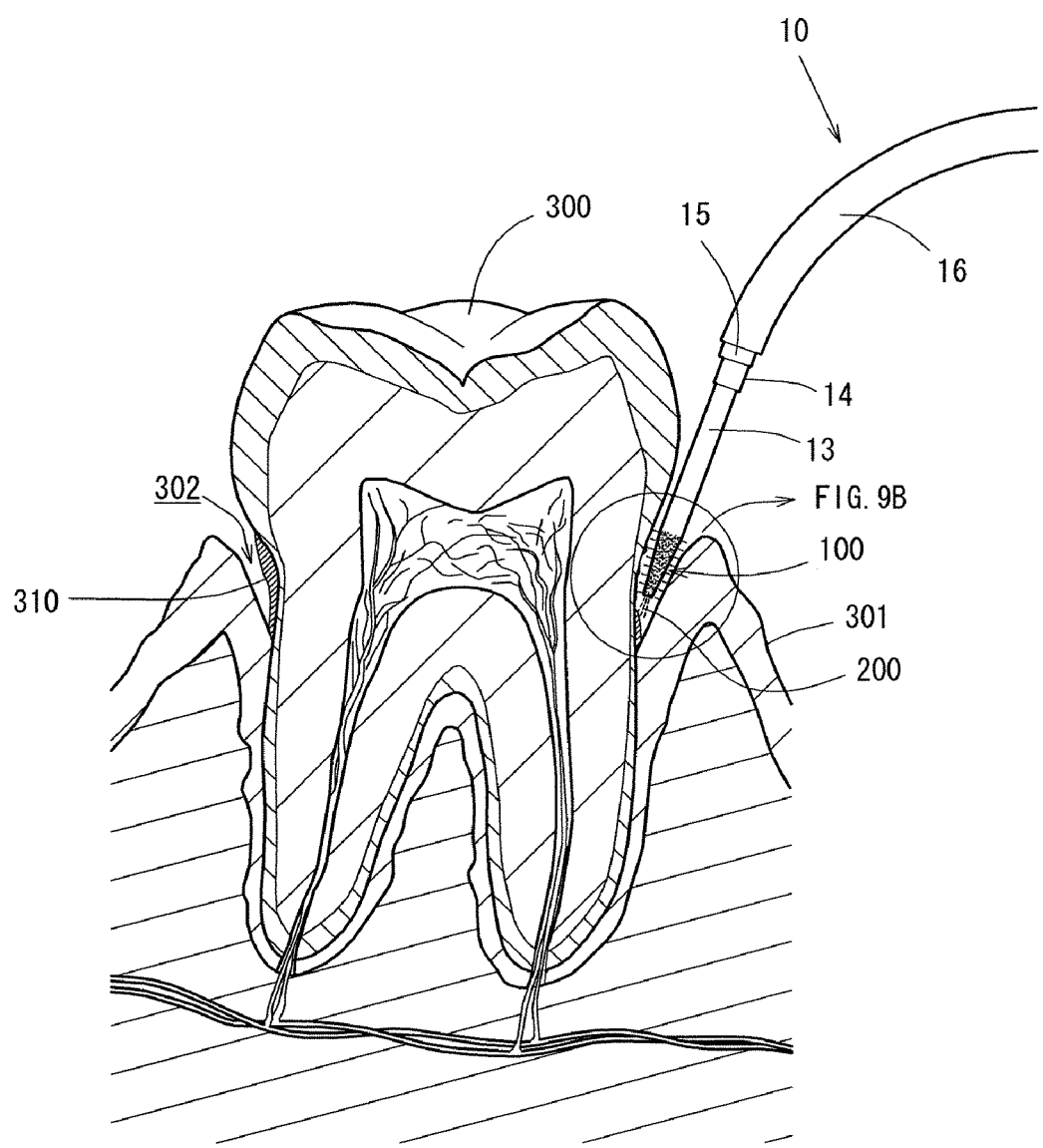
FIG. 9A is a view illustrating a state in which a periodontal disease is treated.
Figure 9B:
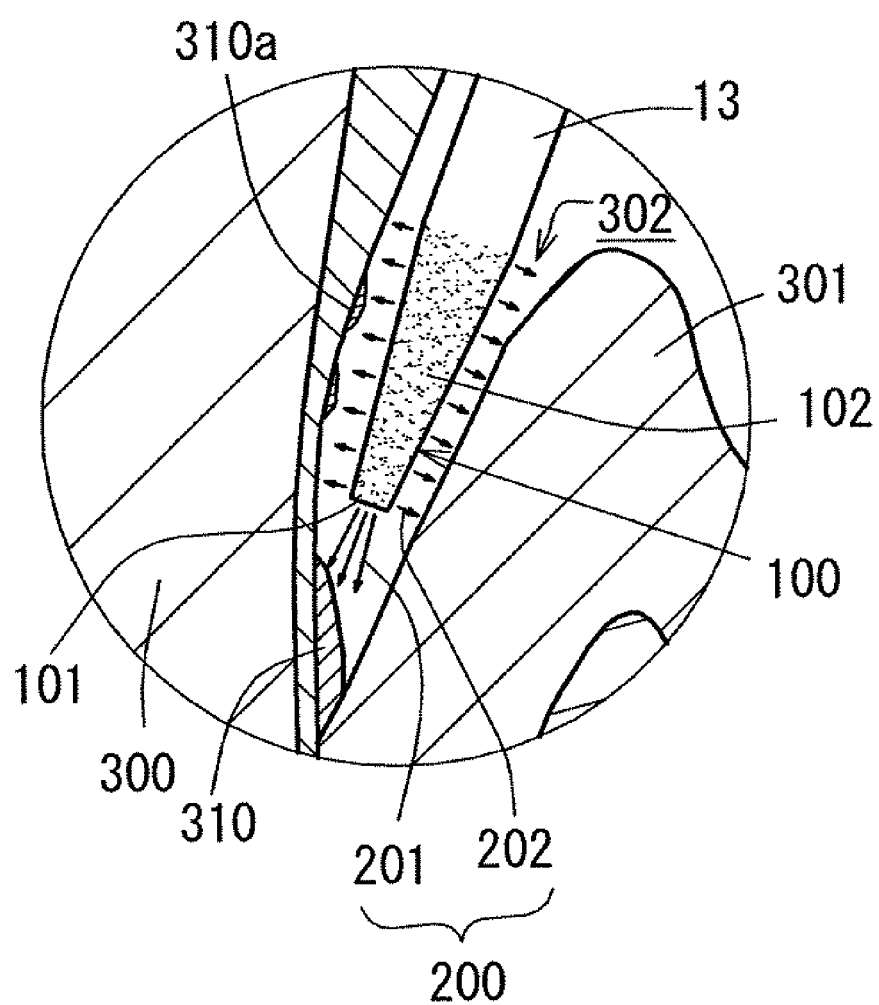
FIG. 9B is a view of an enlarged portion of FIG. 9A.

Treatment of periodontal diseases performed using the dental laser radiation chip 10 including the exit chip 100 for radiating the Er:YAG laser light 200 emitted by the laser light generation source 22 will be described with reference to FIGS. 9A and 9B. FIG. 9A is a view illustrating a state in which a periodontal disease is treated and FIG. 9B is a view of an enlarged portion of FIG. 9A.

Periodontal diseases cause periodontal tissues to be infected with periodontal disease bacteria contained in plaque, cause swelling or bleeding of gum 301, and may finally cause a tooth to be lost. Periodontal diseases are the biggest cause by which the Japanese people lose their teeth.

Plaque, which is a fundamental cause of periodontal diseases, becomes tartar 310 after a certain time period, which cannot be removed by brushing. The tartar 310 causes periodontal disease bacteria to grow and thus aggravates the periodontal diseases.

Tartar formed on a surface of a tooth 300 which is not covered with the gum 301 can be removed by a specified tool such as a scaler or the like. However, it is difficult to remove the tartar 310 formed below the edge of the gum 31, namely, in a periodontal pocket 302 which is a gap between the gum 301 and the tooth 300.

In addition, when the gum 301 suffers from a periodontal disease and is swollen, the gum 301 is separated from the tooth 300. As a result, the periodontal pocket 302 becomes deeper, and it becomes more difficult to remove the plaque and the tartar 310 accumulated in the periodontal pocket 302. When treating a periodontal disease, disinfection for killing the periodontal disease bacteria which cause the periodontal disease also needs to be done at the same time.

In a slight case of periodontal disease, the depth of the periodontal pocket 302 is about 2 to 5 mm. In a serious case of periodontal disease, the depth of the periodontal pocket 302 is 5 mm or greater. In such a serious case of periodontal disease in which the depth of the periodontal pocket 302 is 5 mm or greater, the tooth is loose and plaque is more easily accumulated. This promotes the progress of the periodontal disease, and as a result, the tooth may be lost.

When using the dental laser radiation chip 10 having the exit tip 100 for treating such a periodontal disease, as shown in FIG. 9A, the exit tip 100 of the dental laser radiation chip 10 is inserted into the periodontal pocket 302 and the Er:YAG laser light 200 is radiated from the exit tip 100.

More specifically, as shown in the enlarged portion FIG. 9B, the forward laser light 201 is radiated from the circular tip face 101 to remove the tartar 310 formed on a side surface of the tooth 300 inside the periodontal pocket 302. At this point, the forward laser light 201 is radiated in a direction along the surface of the tooth 300. Therefore, the tartar 310 formed on the surface of the tooth 300 can be removed as being chipped off.

As shown in the enlarged portion FIG. 9B, the side laser light 202 is radiated from the inclining side face 102 to remove dregs 310a left after the tartar 310 is removed by the forward laser light 201 and also to disinfect the surface of the tooth 300 and an inner surface of the gum 301 after the tartar 310 is removed.

At this point, the side laser light 202 is radiated in a wide area substantially perpendicular to the surface of the tooth 300 and the inner surface of the gum 301. Therefore, bacteria concealed in a huge number of craters (not shown) on the surface of the tooth 300 can be killed by disinfection, and also the surface of the tooth 300 after the tartar is removed can be planed (smoothed). More specifically, a huge number of convexed and concaved portions are formed on the surface of the tooth 300 after the tartar 310 is removed, but these convexed and concaved portions can be smoothed out. This is specifically referred to as "root planing".

In this manner, the exit tip 100 having a shape of frustum of cone tapering forward in the direction of the axis L is inserted into the narrow and deep periodontal pocket 302. The forward laser light 201 having a high energy density is radiated from the mirror-surface-finished circular tip face 101 forward in the direction of the axis, and also the side laser light 202 is radiated from the rough-surface-finished inclining side face 102 over a wide area in a radial direction with respect to the axis L. Due to this, the removal of the tartar 310, the disinfection to kill the bacteria concealed in the tooth 300 and the gum 301, which is a soft tissue, and the planing of the surface of the tooth 300 can be performed at the same time.

More specifically, the exit tip 100 of the dental laser radiation chip 10 is formed to have a shape of frustum of cone tapering forward in the direction of the axis L, and the circular tip face 101 from which the laser light is to be radiated forward in the direction of the axis L is mirror-surface-finished. Due to this, the Er:YAG laser light 200 having a high absorbability to water and a relatively high degree of safety can be radiated forward in the direction of the axis L as the forward laser light 201 having a high energy density.

Due to this, a superb effect of removing the tartar 310 can be provided. In the case where unhealthy granulation (not shown) is made in the periodontal pocket 302, the unhealthy granulation may be removed by the forward laser light 201 like the tartar 310.

Since the inclining side face 102 which is a part of the shape of tapering frustum of cone is rough-surface-finished, the Er:YAG laser light 200 is scattered by the convexed and concaved portions of the inclining side face 102 formed by roughening. Therefore, the side laser light 202 having a low energy density can be radiated over a wide area in a radial direction with respect to the axis L.

Due to this, a disinfection effect over a wide area can be provided without unnecessarily damaging the gum 301, which is a soft tissue, and also the dregs 310a left after the tartar 310 is removed can be removed. In addition, the surface of the tooth 300 after the tartar is removed can be planed (smoothed).

In this manner, the dental laser radiation chip 10 having the exit tip 100 can efficiently provide treatment effects on the tooth 300 and the gum 301, which is a soft tissue.

The circular tip face 101 is mirror-surface-finished to have a surface roughness of 0.1 μm or less, for example, 0.008 μm and the inclining side face 102 is rough-surface-finished to have a surface roughness of 0.2 μm or greater and 20 μm or less, for example, 0.4 μm. Therefore, treatment effects can be efficiently provided on the tooth 300 and the gum 301, which is a soft tissue, more certainly.

More specifically, the circular tip face 101 is mirror-surface-finished to have a surface roughness of 0.1 μm or less. Due to this, the forward laser light 201 having a higher energy density can be radiated forward in the direction of the axis L.

Furthermore, in the case where the circular tip face 101 is mirror-surface-finished to have a surface roughness of greater than 0.1 μm, the Er:YAG laser light 200 is scattered by the microscopic convexed and concaved portions having a surface roughness of greater than 0.1 μm formed on the surface of the circular tip face 101 and so laser light having a desired energy density cannot be radiated.

By contrast, by mirror-surface-finishing the circular tip face 101 to have a surface roughness of 0.1 μm or less, for example, 0.008 μm, the scattering of the Er:YAG laser light 200 on the surface of the circular tip face 101 is suppressed, and the forward laser light 201 having a higher energy density and so having a superb performance of removing tartar and unhealthy granulation can be radiated more certainly.

The inclining side face 102 is rough-surface-finished to have a surface roughness of 0.2 μm or greater and 20 μm or less, for example, 0.4 μm. Therefore, the side laser light 202 having an energy density suitable to perform disinfection and planing without unnecessarily damaging the gum 301, which is a soft tissue, can be radiated over a sufficiently wide area due to the convexed and concaved portions of the size range mentioned above which are formed on the surface of the inclining side face 102.

More specifically, in the case where the inclining side face 102 is rough-surface-finished to have a surface roughness of less than 0.2 μm, the laser light is not scattered sufficiently due to the convexed and concaved portions having a surface roughness of less than 0.2 μm formed on the surface of the inclining side face 102, and so the laser light having an energy density reduced to a level at which the gum 301, which is a soft tissue, is not unnecessarily damaged cannot be radiated over a wide area.

By contrast, in the case where the inclining side face 102 is rough-surface-finished to have a surface roughness of greater than 20 μm, the laser light is excessively scattered due to the convexed and concaved portions on the inclining side face 102. As a result, the energy density is reduced, and so laser light having desired effects of disinfection and planing cannot be radiated.

Accordingly, by rough-surface-finishing the inclining side face 102 to have a surface roughness of 0.2 μm or greater and 20 μm or less, for example, 0.4 μm, laser light having an energy density suitable to perform disinfection and planing without unnecessarily damaging the gum 301, which is a soft tissue, can be radiated over a sufficiently wide area.

The exit tip 100 of the dental laser radiation chip 10 has a shape of frustum of cone having a height H of 2 mm or greater and 5 mm or less, for example, 3 mm in the direction of the axis and a cone angle α of 5 degrees or greater and 20 degrees or less, for example, 11 degrees. Due to this, the exit tip 100 of the dental laser radiation chip 10 can be inserted into the narrow and deep periodontal pocket 302 to radiate the Er:YAG laser light 200 having sufficient effects of removing tartar and unhealthy granulation, of disinfection and of planing.

More specifically, since the height H of the shape of frustum of cone in the direction of the axis is set to 2 mm or greater and 5 mm or less, for example, 3 mm, the exit tip 100 of the dental laser radiation chip 10 can be inserted into the periodontal pocket 302 having a depth of about 2 to 5 mm to radiate the Er:YAG laser 200 and thus realize efficient treatment.

Furthermore, in the case where the height H of the exit tip 100 is set to less than 2 mm, the exit tip 100 cannot be inserted deeply into the periodontal pocket 302. Therefore, the forward laser light 201 radiated from the circular tip face 101 cannot reach the vicinity of the bottom of the narrow and deep periodontal pocket 302, and so sufficient treatment cannot be performed. In addition, since the area size of the inclining side face 102 is decreased, the amount of radiation of the side laser light 202 is decreased and so sufficient effects of disinfection and planing cannot be provided.

By contrast, in the case where the height of the exit tip 100 is greater than 5 mm, the area size of the inclining side face 102 is increased. Therefore, the amount of the side laser light 202 radiated from the inclining side face 102 is increased, and so the amount of radiation of the forward laser light 201 radiated from the circular tip face 101 which has a superb performance of removing tartar and unhealthy granulation is decreased.

Accordingly, by setting the height H of the shape of frustum of cone in the axial direction to 2 mm or greater and 5 mm or less, the exit tip 100 can be inserted into the periodontal pocket 302 having a depth of about 2 to 5 mm and so the Er:YAG laser light 200 having sufficient effects of removing tartar and unhealthy granulation, of disinfection and of planing can be radiated to realize efficient treatment.

In addition to setting the height H of the shape of frustum of cone in the axial direction to 2 mm or greater and 5 mm or less, the cone angle α of the shape of frustum of cone is set to 5 degrees or greater and 20 degrees or less, for example, 11 degrees. Due to this, the exit tip can be inserted into the narrow and deep periodontal pocket 302 to perform an operation certainly and improve the durability.

More specifically, in the case where the height H of the exit tip 100 is set to the range described above and the cone angle α of the shape of frustum of cone is set to less than 5 degrees, a required area size of radiation from the circular tip face 101 cannot be obtained, and so the amount of radiation of the forward laser light 201 having a superb performance of removing tartar and unhealthy granulation is decreased. In the case where the cone angle α of the exit tip 100 having a shape of frustum of cone is less than 5 degrees, the exit tip 100 of the dental laser radiation chip 10 is excessively thin and a sufficient durability against repeated operations cannot be provided.

By contrast, in the case where the cone angle α of the exit tip 100 having a shape of frustum of cone is set to greater than 20 degrees, the exit tip 100 of the dental laser radiation chip 10 is excessively thick and cannot be inserted up to the vicinity of the bottom of the narrow and deep periodontal pocket 302. Therefore, the forward laser light 201 having a high energy density does not reach the vicinity of the bottom of the periodontal pocket 302, and so the performance of removing tartar and unhealthy granulation is deteriorated.

In this manner, by setting each of the height H and the cone angle α of the exit tip 100 having a shape of frustum of cone to the above-described range, the durable exit tip 100 can be inserted up to the vicinity of the bottom of the narrow and deep periodontal pocket 302. Therefore, the forward laser light 201 having a superb performance of removing tartar and unhealthy granulation can be radiated from the circular tip face 101, and the side laser light 202 having sufficient effects of disinfection and planing can be radiated from the inclining side face 102. Thus, efficient treatment which provides an effect of removing tartar and unhealthy granulation, an effect of disinfection and an effect of planing at the same time can be performed.

Since the exit tip 100 of the dental laser radiation chip 10 has a shape of frustum of cone, there is no directivity with respect to the axial direction which might otherwise be caused due to the shape of the exit tip 100, and the exit tip 100 is easily shaped along the surface of the tooth 300, especially the surface of the root of the tooth. Thus, the operability in the periodontal pocket 302, which is a narrow operation site, can be improved.

As a result of performing clinical tests on the above-mentioned effects, the evaluations as shown in Table 1 were obtained.

The circular tip face 101 is flat in a direction perpendicular to the axis L. Alternatively, the circular tip face 101 may be slightly inclined with respect to the flat circular tip face 101. Due to this, the forward laser light 201 can be radiated in a desired radiation direction in addition to the effects of the dental laser radiation chip 10 described above being provided.

Still alternatively, the circular tip face 101 may be curved, i.e., convexed or concaved toward the axis L. Due to this, the forward laser light 201 radiated from the circular tip face 101 can be collected to further improve the energy density or, by contrast, can be scattered to reduce the energy density, so that the forward laser light 201 is radiated at a desired energy

TABLE 1

| | Operator A | Operator B | Operator C | Operator D | Operator E |
|---|---|---|---|---|---|
| Comments | Performance of removing tartar, granulation, dregs attached to the surface of the root is superior to that of the conventional chips Well received by the patients, and thanked by the patient in a case of arborization. | Very easy to use Can remove tartar and unhealthy granulation well The tip of the chip can be easily inserted into the pocket | Very easy to use Highly effective to remove unhealthy granulation and dregs attached to the surface of the root Adherence of the gum after treatment is good →The inside of the pocket is disinfected well | The tip of the chip is flat, and so the chip is not much worn by disinfection of the inside of the periodontal pocket and the treatment is not very painful to the patient | Unhealthy granulation is removed very well |
| Case | Removal of tartar Crettage on arborization Removal of unhealthy granulation Disinfection of the pocket exceeding 5 mm | Removal of relatively large pieces of tartar in the pocket Simple incision of the gum Incision of bone Crettage after odontectomy Flap surgery | Flap surgery Periodontal surgery Root planing Non-Flap radiation to the inside of the pocket | Radiation to the inside of the pocket Removal of tartar Removal of unhealthy granulation | Removal of tartar Removal of unhealthy granulation |
| Durability | About 100 teeth | About 100 teeth | | | |

The following has been confirmed. Use of the dental laser radiation chip 10 including the exit tip 100 of a shape of frustum of cone, which has the mirror-surface-finished circular tip face 101 and the rough-surface-finished inclining side face 102 for treatment of periodontal diseases, makes it possible to efficiently perform the removal of unhealthy granulation and the removal of the tartar 310 in the narrow and deep periodontal pocket 302 using the forward laser light 201 and also perform the disinfection and planing over a wide area using the side laser light 202. This makes both of the operator and the patient more satisfied.

In this example, the fiber 13 has a diameter of 600 μm and the circular tip face 101 thereof has a diameter D of 400 μm. Alternatively, the fiber 13 may have a diameter of 800 μm and the circular tip face 101 thereof may have a diameter D of 600 μm.

The exit tip 100 has a shape of frustum of cone, but may have a shape of frustum of triangular pyramid, a shape of frustum of quadrangular pyramid, or a shape of frustum of polygonal pyramid. In such a case also, the effect of removing tartar and unhealthy granulation, the effect of disinfection and the effect of planing can be provided at the same time, like in the case of the above-described dental laser radiation chip 10.

density, in addition to the effects of the dental laser radiation chip 10 described above being provided.

Substantially the same is true with the inclining side face 102. The inclining side face 102 is flat as seen from the side. Alternatively, the inclining side face 102 may be convexed outward in a radial direction with respect to the axis L as seen from the side or concaved inward in the radial direction with respect to the axis L as seen from the side. In such a case also, the side laser light 202 of a desired energy density can be radiated from the inclining side face 102 in addition to the effects of the dental laser radiation chip 10 described above being provided.

In addition, in this example, the dental laser radiation chip 10 includes the chip main body 12 having the curved part 12a and the straight part 12b. Alternatively, as shown in FIGS. 10A and 10B, a dental laser radiation chip 10' including a chip main body 12 which is straight may be used.

Instead of the dental laser radiation chip 10 or 10' which is of a probe type, a straight chip attachable to a head of the hand piece in a substantially perpendicular direction with respect to the longitudinal axis of the hand piece, for example, a chip like a cutting tool attachable to a head of an air turbine hand piece (see FIG. 3 of Japanese Laid-Open Patent Publication No. 07-155335) may be used.

The elements of the present invention and the elements in the above-described embodiment correspond as follows.

The optical fiber of the present invention corresponds to the fiber 13;

the laser light having a wavelength of around 3 μm corresponds to the Er:YAG laser light 200;

the tip section corresponds to the exit tip 100; and the tip face corresponds to the circular tip face 101.

However, the present invention is not limited to having the structure of the above-described embodiment, and may be carried out in various other embodiments.

For example, in the above description, the dental laser radiation chip 10 having the exit tip 100 is used for treatment of periodontal diseases. Needless to say, the dental laser radiation chip 10 is usable for treatment of other dental applications including oral surgery.

DESCRIPTION OF THE REFERENCE NUMERALS

- 10 . . . Dental laser radiation chip
- 13 . . . Fiber
- 100 . . . Exit tip
- 101 . . . Circular tip face
- 102 . . . Inclining side face
- 131 . . . Fiber center section
- 132 . . . Jacket
- 200 . . . Er:YAG laser light
- L . . . Axis
- H . . . Height
- α . . . Cone angle

What is claimed is:

1. A dental laser radiation chip, comprising:
   an optical fiber including a fiber center section having a core and a clad and also including a jacket for covering the fiber center section, the dental laser radiation chip being for radiating laser light having a wavelength of around 3 μm;

wherein a tip section of the dental laser radiation chip has a shape of frustum tapering forward in an axial direction, the shape of frustum including a tip face from which the laser light is to be radiated forward in the axial direction and an inclining side face from which the laser light is to be radiated in a radial direction with respect to the axial direction; and wherein the tip face is mirror-surface-finished, and the inclining side face is rough-surface-finished.

2. The dental laser radiation chip according to claim 1,
   wherein the shape of frustum is a shape of frustum of cone;
   wherein the mirror-surface-finished face has a surface roughness of 0.1 μm or less; and
   wherein the rough-surface-finished face has a surface roughness of 0.2 μm or greater and 20 μm or less.

3. The dental laser radiation chip according to claim 1,
   wherein the tip section has a shape of frustum having a height in the axial direction of 2 mm or greater and 5 mm or less and a cone angle of 5 degrees or greater and 20 degrees or less.

4. The dental laser radiation chip according to claim 2,
   wherein the tip section has a shape of frustum having a height in the axial direction of 2 mm or greater and 5 mm or less and a cone angle of 5 degrees or greater and 20 degrees or less.

\* \* \* \* \*